United States Patent [19]

Plant et al.

[11] Patent Number: 4,654,330

[45] Date of Patent: Mar. 31, 1987

[54] CERTAIN 2-(PYRIDYL OR THIENYL)-1,3,4-OXADIAZOLE-5-METHYLENE-THIO-PHOSPHATES, THIO ANALOGUES THEREOF COMPOSITIONS CONTAINING SAME AND PESTICIDAL USE

[75] Inventors: Howard L. Plant, Milford; Richard R. Regis, Harwinton; Richard C. Moore, Wallingford, all of Conn.

[73] Assignee: Uniroyal Chemical Company, Inc., Middlebury, Conn.

[21] Appl. No.: 592,688

[22] Filed: Mar. 23, 1984

[51] Int. Cl.$^4$ .............................. C07F 9/58; C07F 9/65; A01N 43/40; A01N 43/82

[52] U.S. Cl. ................................ 514/89; 514/92; 546/22; 548/143

[58] Field of Search .................. 548/112, 143; 546/22; 514/89, 92

[56] References Cited

U.S. PATENT DOCUMENTS

| | | | |
|---|---|---|---|
| 3,432,519 | 3/1969 | Metivier et al. | 548/119 |
| 3,502,668 | 3/1970 | Palazzo et al. | 548/143 |
| 3,690,858 | 9/1972 | Dahle et al. | 71/92 |

FOREIGN PATENT DOCUMENTS 708460 11/1970 South Africa ...................... 548/112

OTHER PUBLICATIONS

Suzuki et al., Chem. Abstracts, vol. 86, No. 9, Abst. No. 55451d, Feb. 28, 1977.

Primary Examiner—Alan L. Rotman
Attorney, Agent, or Firm—William E. Dickheiser

[57] ABSTRACT

A compound of the formula

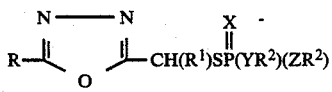

wherein R is allyl, halocyclopropyl, $C_3$-$C_5$ alkoxycarbonylmethyl, $C_7$-$C_9$ aralkyl, styryl, phenyl, naphthyl, furanyl, pyridyl, thienyl, phenyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro or $C_7$-$C_9$ aralkyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro; $R^1$ is hydrogen, $C_1$-$C_3$ alkyl, $C_7$-$C_9$ aralkyl, phenyl, $C_7$-$C_9$ aralkyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro or phenyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro, however, if R is substituted phenyl or substituted $C_7$-$C_9$ aralkyl, then $R^1$ cannot be hydrogen; $R^2$ is $C_1$-$C_4$ alkyl, however, if R or $R^1$ is 4-chlorophenyl, $R^2$ cannot be isopropyl; and X, Y and Z are the same or different and are oxygen or sulfur, is disclosed. A method is provided for protection against pests by employing a pesticidally effective amount of the compound above. A composition comprising the compound above and an inert carrier therefor, for pesticidal use, is also taught.

The disclosure also recites a compound of the formula

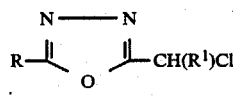

where R and $R^1$ have the meanings of the first mentioned compound. The compound, effective as an intermediate in the synthesis of the above compound, is produced by the reaction of a compound of the formula

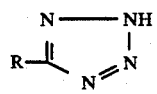

where R has the meanings given above with a compound of the formula

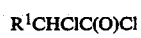

$R^1$CHClC(O)Cl where $R^1$ has the meanings given above.

15 Claims, No Drawings

CERTAIN 2-(PYRIDYL OR THIENYL)-1,3,4-OXADIAZOLE-5-METHYLENE-THIO-PHOSPHATES, THIO ANALOGUES THEREOF COMPOSITIONS CONTAINING SAME AND PESTICIDAL USE

BACKGROUND OF THE INVENTION

1. Field of the Invention

The instant invention is directed to a class of oxadiazolemethylphosphates. More specifically, the instant invention is directed to a class of oxadiazolemethylphosphates useful as pesticides and certain intermediates for making same.

2. Background of the Prior Art

Harmful pests, especially insects, nematodes and arachnids, attack a wide variety of ornamental and agricultural plants. These pests inflict damage by consuming foliage, withdrawing vital juices from the plants, secreting toxins and transmitting diseases. There is thus a continuing need to develop new means to control these pests.

Oxadiazole compounds carrying phosphorous containing moieties as substituents are known as useful pesticides:

U.S. Pat. No. 3,432,519, Mar. 11, 1969 (Metivier et al) discloses substituted 1,2,4-oxadiazole insecticides and acaracides which carry a chloro-substituted phenyl in the 3-position and a phosphorylmethyl moiety in the 5-position.

U.S. Pat. No. 3,192,103, June 29, 1965 (Sousa et al.) teaches the use of disubstituted oxadiazoles as nematocides. However, this class of compounds does not include any phosphorous containing substituents.

German Offenlegungsschrift No. 1,963,672 is directed to substituted oxadiazolemethyl dithiophosphates which are recited to be useful as insecticides. The class of compounds disclosed in this reference include the requirement that the phosphorous and the oxadiazole moieties be linked by a methylene group.

Chemical Abstracts 86:55451, an abstract of a Japanese patent publication, deals with a similar class of compounds disclosed in the above mentioned German Offenlegungsschrift. That is, this reference recites the use of substituted oxadiazole dithiophosphates wherein the phosphate and oxadiazole moieties are linked by a methylene group which class of compounds are useful as insecticides.

SUMMARY OF THE INVENTION

A new class of compounds providing unexpected superior performance as a pesticide in the control of such pests as insects, nematodes, and acarids has now been found. These compounds may be applied directly or as compositions in combination with a suitable carrier.

In accordance with the instant invention a compound having the formula

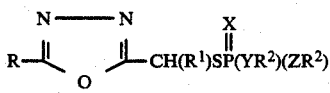

where R is allyl, halocyclopropyl, $C_3$-$C_5$ alkoxycarbonylmethyl, $C_7$-$C_9$ aralkyl, styryl, phenyl, naphthyl, furanyl, pyridyl, thienyl, phenyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro or $C_7$-$C_9$ aralkyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro; $R^1$ is hydrogen, $C_1$-$C_3$ alkyl, $C_7$-$C_9$ aralkyl, phenyl, $C_7$-$C_9$ aralkyl substituted with halogen $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro or phenyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro, however, if R is substituted phenyl or substituted $C_7$-$C_9$ aralkyl, then $R^1$ cannot be hydrogen; $R^2$ is $C_1$-$C_4$ alkyl, however, if R or $R^1$ is 4-chlorophenyl, $R^2$ cannot be isopropyl; and X, Y and Z are the same or different and are oxygen or sulfur, is disclosed.

Also, in accordance with the present invention a compound having the structural formula

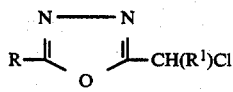

where R and $R^1$ have the meanings given above are taught.

In further accordance with the instant invention, a method for controlling pests using the compounds recited above is taught.

In still further accordance with the instant invention a composition comprising the compound recited above with a carrier therefor is set forth.

In yet further accordance with the instant invention, processes for producing the compound recited above are provided. In these processes an alpha-halo acyl halide is reacted with a tetrazole in a dry hydrocarbon solvent at a temperature in the range of from 100° to 140° C., resulting in the formation of a 2-halomethyl-1,3,4-oxadiazole. The 2-halomethyl 1,3,4-oxadiazole is converted to a dialkyldithiophosphate by warming the ammonium or metal salt of the dithiophosphate in an acetone or acetonitrile solution.

DETAILED DESCRIPTION

The compounds of the instant invention have the formula

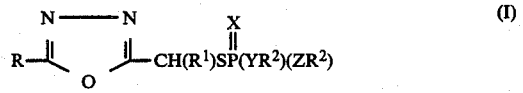

(I)

where R is allyl, halocyclopropyl, $C_3$-$C_5$ alkoxycarbonylmethyl, $C_7$-$C_9$ aralkyl, styryl, phenyl, naphthyl, furanyl, pyridyl, thienyl, phenyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro or $C_7$-$C_9$ aralkyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro; $R^1$ is hydrogen, $C_1$-$C_3$ alkyl, $C_7$-$C_9$ aralkyl, phenyl, $C_7$-$C_9$ aralkyl substituted with halogen, $C_1$-$C_4$ alkyl, trihalomethyl, $C_1$-$C_4$ alkoxy, trihalomethoxy, trihalomethylthio, $C_1$-$C_4$ alkylthio, phenyl, phenoxy, cyano or nitro or phenyl substituted with halogen, $C_1$-$C_4$ alkyl, trihalomethyl, $C_1$-$C_4$ alkoxy, trihalomethoxy, trihalomethylthio, $C_1$–$C_4$ alkylthio, phenyl, phenoxy, cyano or nitro, however, if R is substituted phenyl or substituted $C_7$–$C_9$ aralkyl, then $R^1$ cannot be hydrogen; $R_2$ is $C_1$–$C_4$ alkyl, however, if R or $R^1$ is 4-chlorophenyl, $R^2$ cannot be isopropyl; and X, Y and Z are the same or different and are oxygen or sulfur.

More preferably, the compound of this invention has the structural formula (I) where R is halocyclopropyl, t-butyl, pyridyl, thienyl or phenyl substituted with methyl, chlorine, trifluoromethyl or nitro; $R^1$ is hydrogen, methyl or phenyl; $R^2$ is ethyl; X is sulfur; Y is oxygen; and Z is oxygen.

Still more preferably, the compounds of this invention have the structural formula (I) and R, $R^1$ and $R^2$ have the following corresponding meanings:

| R | $R^1$ | $R^2$ |
|---|---|---|
| 1-methyl-2,2-dichlorocyclopropyl | hydrogen | ethyl |
| 1-methyl-2,2-dichlorocyclopropyl | phenyl | " |
| 4-chlorophenyl | methyl | " |
| 2-methylphenyl | phenyl | " |
| 4-trifluoromethylphenyl | methyl | " |
| 4-nitrophenyl | methyl | " |
| pyrid-2-yl | hydrogen | " |
| pyrid-3-yl | methyl | " |
| pyrid-4-yl | methyl | " |
| t-butyl | phenyl | " |

In addition to compound I, which as will be discussed below is a pesticide, the present invention is directed to a class of compounds having the structural formula

 (II)

where R is allyl, halocyclopropyl, $C_3$–$C_5$ alkoxycarbonylmethyl, $C_7$–$C_9$ aralkyl, styryl, phenyl, naphtyl, furanyl, pyridyl, thienyl, phenyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro or $C_7$–$C_9$ aralkyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro; and $R^1$ is hydrogen, $C_1$–$C_3$ alkyl, $C_7$–$C_9$ aralkyl, phenyl, $C_7$–$C_9$ aralkyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro or phenyl substituted with halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro; however, if R is substituted phenyl or substituted $C_7$–$C_9$ aralkyl, then $R^1$ cannot be hydrogen.

More preferably, the intermediate compound of this invention has the structural formula II where R is halocyclopropyl, t-butyl, pyridyl, thienyl or phenyl substituted with methyl, chlorine, trifluoromethyl or nitro; and $R^1$ is hydrogen, methyl or phenyl.

Still more preferably, the intermediate compound of this invention is a compound having the formula I where R and $R^1$ have the corresponding meanings.

| R | $R^1$ |
|---|---|
| 1-methyl-2,2-dichlorocyclopropyl | hydrogen |
| 1-methyl-2,2-dichlorocyclopropyl | phenyl |
| 4-chlorophenyl | methyl |
| 2-methylphenyl | phenyl |
| 4-trifluoromethylphenyl | methyl |
| 4-nitrophenyl | methyl |
| pyrid-2-yl | hydrogen |
| pyrid-3-yl | methyl |
| pyrid-4-yl | methyl |
| t-butyl | phenyl |

Compound I of this invention is generally prepared by reacting a substituted tetrazole with an excess of the substituted chloroacyl chloride in an inert solvent such as xylene by heating and stirring at a temperature of 100° to 140° C. for one to four hours. The reaction may be described by the following equation (wherein R and $R^1$ have the meanings given for compounds (I) and (II):

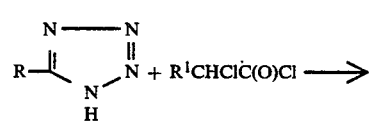

During the heating period, equivalent amounts of HCl and $CO_2$ are removed through an appropriate venting system. Dilution of the residue with chloroform followed by washing with dilute (e.g. 0.01N) sodium hydroxide and water yields a solution of the product. Drying and removal of the solvent provides the intermediate product, compound II, in good to excellent yields.

To obtain compound (I) of the present invention the novel haloalkyl oxadiazole (compound II) is reacted with an excess of salt of a dialkoxy dithiophosphate in a solvent such as acetone or acetonitrile for a period of six to twenty-four hours at 10° to 70° C., as indicated in the equation below.

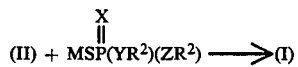

It is noted that, R, $R^1$, $R^2$, X, Y and Z have the meanings given above for compound (I). M is an alkali metal ion or $NH_4^+$. If M is an alkali metal ion, it is preferably $Na^+$ or $K^+$.

After removal of the solvent (under reduced pressure), the residue is extracted with a polychlorinated hydrocarbon such as dichloromethane or chloroform and is subsequently washed with a dilute (e.g. 0.01N) solution of hydrochloric acid and water. After drying and evaporation of the solvent, the product is isolated in good to excellent yields.

The species within the definition of Compound (I) of this invention are employed as an insecticide, a nematocide and/or an acaricide. The compounds of this invention may be used alone, that is, neat, in combination with a liquid carrier in which it is dissolved or suspended or mixed with or absorbed on a solid carrier. It is emphasized that the carrier itself is inert in terms of providing insecticidal, nematocidal or acaricidal effect.

In the case where a liquid inert carrier is employed, the active compound of the instant invention is dissolved or suspended therein. Suitable carriers within the contemplation of this invention include water, aliphatic alcohols, aromatic solvents such as substituted and unsubstituted phenol, benzene, kerosene, toluene or xylene.

In the preferred embodiment wherein the active compound of this invention is combined with a liquid carrier, and the carrier is not a solvent for the active compound of this invention, then it is preferred to employ one or more surface active agents. Obviously, the most common dispersing agent, that is, non-solvent, for the compounds of this invention is water. In those cases, the active compound of this invention is applied as an emulsion. The active compound of the invention is dissolved in a suitable organic solvent of the type mentioned above. Thereafter, the organic solution is added to water containing a surface-active agent which may be an anionic, non-ionic or cationic surface-active material.

Optionally, the compounds of the instant invention are combined with water to form a dispersion in the absence of an organic solvent. Again, surface-active dispersing agents are employed. Surface-active agents are well known in the art. For example, U.S. Pat. No. 2,547,734 provides detailed examples of such agents employed in the emulsion or dispersion type compositions of this invention.

As indicated above, the compounds of the instant invention may also be combined with solid inert carriers such as the mineral silicates, e.g., mica, talc, prophyllite and clays. Other solid carriers within the contemplation of this invention include vermiculite, charcoal and corn cobs. Solid compositions of the instant invention are applied by well known methods in the art such as broadcasting, side dressing, soil incorporation or seed treatment.

In yet another preferred embodiment of the instant invention the active compound (I) of the instant invention is combined with a powdered solid carrier and dispersed in water provided with a surface-active dispersing agent. The suspension thus formed is applied by the methods recited above for dispersal of solid compositions, that is, broadcasting, side dressing, soil incorporation or seed treatment.

In yet another method for applying the pesticidal compositions of the instant invention, solutions for aerosol treatment may be prepared. Their preparation involves dissolving the compound (I) of this invention directly in the aerosol solvent which is liquid at elevated pressures. The aerosol method involves releasing the aerosol solution in the atmosphere at which pressure the carrier is gaseous. Alternatively, the aerosol solution may be prepared by first dissolving the compound (I) in a less volatile solvent and then admixing the thus formed solution with a highly volatile liquid aerosol carrier.

In order to provide additional protection, it is within the contemplation of this invention for the compound (I) of this invention to be admixed with carriers which are active themselves, i.e., insecticides, acaricides, fungicides or bacteriacides.

The pesticidal compositions of the instant invention discussed above include sufficient concentration of compound (I) to be effective for the particular method of control. The required concentration of the active agent, compound (I), varies widely. Typically, the concentration range of compound (I) is from 0.1 to 95% by weight. Spray dilutions can contain a concentration within the above-recited range or even lower amounts, a few parts per million, to even full strength. Concentrations per unit area can vary from 0.01 to 50 pounds per acre, preferably, from 0.1 to 10 pounds per acre.

To control pests, the compound of this invention may be applied to the pests directly, to the plants upon which they feed, to the soil or other medium in which the pests live or combinations of the three. In the case of insecticides, all three methods may be employed. That is, compound (I) may be applied as a foliar insecticide or soil insecticide. In the case of the use of the compound (I) as an acaricide, it is preferred that the compound be applied as a foliar acaricide. On the other hand, in the utilization of compound (I) as a nematocide it is preferred that the application means be by disposal in the soil.

The following examples are given to illustrate the instant invention. Therefore, no express or implied limitation of the invention to these examples should be assumed.

EXAMPLE 1

Preparation of
2-(2-Pyridyl)-5-(1-(O,O-diethyldithiophosphoryl)ethyl)-1,3,4-oxadiazole (Cpd. No. 43)

61 g of 2-(2-pyridyl)-5-(1-chloroethyl)-1,3,4-oxadiazole (0.27 mol) and 63 g of the ammonium salt of O,O-diethyldithiophosphate was slurried in 150 ml of acetone. The well stirred mixture was warmed at 50° C. for four (4) hours and then stirred overnight at ambient temperature. The salt was filtered off and washed with 25 ml of acetone. The acetone solution was reduced to an amber oil that was taken up in 200 ml of chloroform and washed thoroughly by shaking with three 200 ml portions of water. The chloroform solution was dried over anhydrous sodium sulfate followed by vacuum evaporation on a hot water bath yielding 99 g of product as an amber oil (98% theory). The product of this synthesis was verified by IR and NMR analyses.

EXAMPLE 2

Preparation of
2-(3-Trifluorotolyl)-5-alpha-(O,O-diethyldithiophosphoryl-1,3,4-oxadiazoles (Cpd. No. 33)

6.8 g (0.02 mol) of 2-(3-trifluorotolyl)-5-(alphachlorobenzyl)-1,3,4-oxadiazole and 4.2 g (0.021 mol) of the ammonium salt of O,O-diethyldithiophosphate were slurried in 35–40 ml of acetonitrile and warmed to 50°–60° C. for two hours. The heat was removed and the mixture stirred overnight at ambient temperature. The salt was removed by filtration and the solvent under vacuum. The resulting oil was dissolved in 75 ml of chloroform and washed with three 80 ml portions of water. The chloroform layer was dried over anhydrous sodium sulfate and evaporated under vacuum to 9 g of product (92% theory). The product of this preparation was verified by IR and NMR analyses.

EXAMPLE 3

Preparation of
2-(2,2-Dichloro-1-methylcyclopropyl)-5-(1-(O,O-diethyldithiophosphoro)ethyl)-1,3,4-oxadiazole (Cpd. No. 2)

3.2 g of 2-(2,2-dichloro-1-methylcyclopropyl)-5-(1-chloroethyl)-1,3,4-oxadiazole (0.01 mol) and 2.8 g of the ammonium salt of O,O-diethyldithiophosphate were slurried in 25 ml of acetone and with good stirring warmed to 40°–50° for thirty minutes. After stirring overnight at ambient temperature, the precipitated salt was filtered off and the filtrate reduced to an oil under vacuum. The amber oil was taken up in chloroform and washed twice with water, dried and again reduced under vacuum to 3.5 g of oil (86% theory). The structure was verified by IR and NMR analyses.

Following essentially the procedures outlined above, additional compounds were prepared. They, as well as the compounds synthesized in Examples 1–3, are summarized in Table I below.

TABLE I $$R-\underset{O}{\overset{N-N}{\|}}-CH(R^1)SP(S)(OR^2)_2$$

| Cpd. No. | R | $R^1$ | $R^2$ | m.p. °C. |
|---|---|---|---|---|
| 1 | 1-CH$_3$—2,2-Cl$_2$C$_3$H$_2$ | H | C$_2$H$_5$ | oil |
| 2 | " | CH$_3$ | " | " |
| 3 | " | C$_6$H$_5$ | " | " |
| 4 | " | " | i-C$_3$H$_7$ | " |
| 5 | " | 3-CH$_3$C$_6$H$_4$ | C$_2$H$_5$ | v. oil |
| 6 | " | 4-ClC$_6$H$_4$ | " | " |
| 7 | C$_2$H$_5$OOCCH$_2$ | C$_6$H$_5$ | " | oil |
| 8 | 4-ClC$_6$H$_4$CH$_2$ | CH$_3$ | " | " |
| 9 | " | C$_6$H$_5$ | " | " |
| 10 | 2,6-Cl$_2$C$_6$H$_3$CH$_2$ | " | " | " |
| 11 | C$_6$H$_5$CH(CH$_3$)$_2$ | " | " | " |
| 12 | 4-ClC$_6$H$_4$—CH(CH$_3$)$_2$ | " | " | " |
| 13 | " | " | n-C$_4$H$_9$ | " |
| 14 | C$_6$H$_5$CH=CH— | CH$_3$ | C$_2$H$_5$ | " |
| 15 | C$_6$H$_5$ | C$_6$H$_5$ | " | " |
| 16 | 2-ClC$_6$H$_4$ | " | " | " |
| 17 | 4-ClC$_6$H$_4$ | CH$_3$ | " | v. oil |
| 18 | " | C$_2$H$_5$ | n-C$_4$H$_9$ | oil |
| 19 | " | C$_6$H$_5$ | C$_2$H$_5$ | v. oil |
| 20 | " | " | i-C$_3$H$_7$ | " |
| 21 | " | " | n-C$_4$H$_9$ | oil |
| 22 | " | 4-FC$_6$H$_4$ | C$_2$H$_5$ | v. oil |
| 23 | 3,4-Cl$_2$C$_6$H$_3$ | C$_6$H$_5$ | " | resin |
| 24 | 2-CH$_3$C$_6$H$_4$ | " | " | oil |
| 25 | 3-CH$_3$C$_6$H$_4$ | C$_6$H$_5$ | C$_2$H$_5$ | oil |
| 26 | 4-CH$_3$C$_6$H$_4$ | 4-ClC$_6$H$_4$ | " | v. oil |
| 27 | 4-CF$_3$C$_6$H$_4$ | CH$_3$ | " | 81–83 |
| 28 | " | C$_2$H$_5$ | " | v. oil |
| 29 | " | " | i-C$_3$H$_7$ | " |
| 30 | " | 4-ClC$_6$H$_4$ | C$_2$H$_5$ | " |
| 31 | " | 4-FC$_6$H$_4$ | " | " |
| 32 | 4-CF$_3$C$_6$H$_4$ | 4-CF$_3$C$_6$H$_4$ | " | " |
| 33 | 3-CF$_3$C$_6$H$_4$ | C$_6$H$_5$ | i-C$_3$H$_7$ | oil |
| 34 | " | 4-FC$_6$H$_4$ | n-C$_4$H$_9$ | v. oil |
| 35 | C$_6$H$_5$C$_6$H$_4$ | CH$_3$ | C$_2$H$_5$ | oil |
| 36 | 3,4,5-(CH$_3$O)$_3$C$_6$H$_2$ | C$_6$H$_5$ | C$_2$H$_5$ | 127–128 |
| 37 | 4-NO$_2$C$_6$H$_4$ | CH$_3$ | " | 95–96 |
| 38 | " | C$_6$H$_5$ | " | 92–94 |
| 39 | " | 4-ClC$_6$H$_4$ | " | st. solid |
| 40 | " | 4-CH$_3$C$_6$H$_4$ | " | " |
| 41 | pyrid-2-yl | H | " | oil |
| 42 | " | " | i-C$_3$H$_7$ | " |
| 43 | " | CH$_3$ | C$_2$H$_5$ | " |
| 44 | " | C$_2$H$_5$ | " | " |
| 45 | " | C$_6$H$_5$ | " | " |
| 46 | " | " | i-C$_3$H$_7$ | v. oil |
| 47 | " | " | n-C$_4$H$_9$ | " |
| 48 | " | 4-ClC$_6$H$_4$ | C$_2$H$_5$ | oil |
| 49 | " | 4-FC$_6$H$_4$ | " | v. oil |
| 50 | " | 4-CH$_3$C$_6$H$_4$ | " | oil |
| 51 | " | 2,4-(CH$_3$)$_2$C$_6$H$_3$ | " | " |
| 52 | pyrid-3-yl | H | C$_2$H$_5$ | oil |
| 53 | " | CH$_3$ | " | " |
| 54 | " | C$_6$H$_5$ | " | v. oil |
| 55 | pyrid-4-yl | CH$_3$ | " | oil |
| 56 | " | C$_2$H$_5$ | " | v. oil |
| 57 | " | C$_6$H$_5$ | " | oil |
| 58 | " | 4-FC$_6$H$_4$ | " | v. oil |

TABLE I-continued $$R-\underset{O}{\overset{N-N}{\|}}-CH(R^1)SP(S)(OR^2)_2$$

| Cpd. No. | R | $R^1$ | $R^2$ | m.p. °C. |
|---|---|---|---|---|
| 59 | " | 4-CH$_3$C$_6$H$_4$ | " | " |
| 60 | thien-2-yl | CH$_3$ | " | oil |
| 61 | " | C$_6$H$_5$ | " | v. oil |
| 62 | (CH$_3$)$_3$C | " | " | oil |
| 63 | " | CH$_3$ | " | liquid |

Remarks:
v. = viscous
st. = sticky
Structure and configuration of compounds were confirmed by infrared (IR) and nuclear magnetic (NMR) analyses.

Further compounds within the scope of this invention are prepared having the substituents as indicated in Table II.

TABLE II $$R-\underset{O}{\overset{N-N}{\|}}-CH(R^1)S\overset{X}{\underset{\|}{P}}(YR^2)(ZR^2)$$

| R | $R^1$ | $R^2$ | X | Y | Z |
|---|---|---|---|---|---|
| 2,2-Cl$_2$C$_3$H$_3$ | H | CH$_3$ | O | S | O |
| 3-CNC$_6$H$_5$ | CH$_3$ | C$_2$H$_5$ | S | O | O |
| CH$_3$OOCCH$_2$ | C$_6$H$_5$ | C$_2$H$_5$ | S | O | O |
| 4-FC$_6$H$_4$ | CH$_3$ | CH$_3$ | O | S | O |
| 4-F$_3$CO—C$_6$H$_4$ | C$_6$H$_5$ | C$_2$H$_5$ | S | O | O |
| C$_6$H$_5$ | 3-CHC$_6$H$_4$ | CH$_3$ | S | O | O |
| 4-CH$_3$C$_6$H$_4$CH$_2$ | C$_6$H$_5$ | C$_2$H$_5$ | S | O | O |
| 3,4-Br$_2$C$_6$H$_3$ | C$_6$H$_5$ | C$_2$H$_5$ | S | O | O |
| 4-IC$_6$H$_4$ | C$_2$H$_5$ | CH$_3$ | O | O | O |
| 4-(C$_6$H$_5$O)C$_6$H$_4$ | C$_6$H$_5$ | C$_2$H$_5$ | S | O | O |
| 4-CH$_3$SC$_6$H$_4$ | C$_2$H$_5$ | C$_2$H$_5$ | S | O | O |
| CH$_2$=CHCH$_2$ | 4-CNC$_6$H$_4$ | CH$_3$ | O | O | S |
| C$_6$H$_5$C(CH$_3$)$_2$ | CH$_3$ | C$_2$H$_5$ | S | O | O |

EXAMPLE 4

PESTICIDAL USE OF THE COMPOUNDS OF THIS INVENTION

Organophosphorus compounds within the contemplation of this invention were tested to determine their pesticidal activity against common insects and mites. In these tests those compounds, within the meaning of compound (I), identified as compounds 1–62 were each prepared in a concentration of 6,000 parts per million (ppm) by dissolving 0.6 g of the tested compound in 10 ml of acetone and adding 4 drops of a suitable wetting agent. This solution was diluted to 100 ml by adding water to give the 6,000 ppm suspension.

In certain of the tests a more dilute suspension having a concentration of 3,000 ppm was desired. In those cases an aliquot of the 6,000 ppm suspension was further diluted to yield the 3,000 ppm suspension of the compound.

In yet other tests even more dilute suspensions were required. Thus, to obtain 1,000 ppm and 500 ppm suspensions, the more concentrated suspension was further diluted to obtain the desired dilute concentration.

The tests described above were each repeated with controls in which the active compounds were not provided to obtain a comparison by which the precent control was calculated.

A. Boll Weevil Test

Test formulations of compounds 1-63 at a concentration of 1000 ppm were employed. Two cotton seedlings plants were treated with each formulation by spraying with a spray atomizer. Five adult boll weevils, *Anthonomous grandis*, were placed on plants in each pot one day following treatment. The surviving weevils were counted after five days to determine the percent control.

B. Southern Corn Rootworm Pouch Test

Test formulations of compounds 1-63 at concentrations of 500 or 1000 ppm of the compounds were used. Five ml of the suspension was pipetted onto a paper towel, inserted into a Ziploc [trademark] plastic bag. Two corn seedlings were also soaked in the chemical preparation and placed in the plastic bag. Bags were held for 18 hours before being loaded with 5 corn rootworm, *Diabrotica undecimpunctata*, larvae. After six days, the number of live larvae were noted and the percent control was calculated.

C. Mite One-Day Residual Test

Test suspensions of compounds 1-63 at a concentration of 1000 ppm were employed. Cowpeas, in the first primary leaf stage, were used in the test. Two plants per pot (one primary leaf each) were used for each replicate; two replicates were used for each compound tested. The plants were sprayed with the dispersions using a spray atomizer to thoroughly drench the foliage.

One day following treatment, a circle of tree tanglefoot was placed on the upper surface of the treated leaves and adult mites, *Tetranychus urticae* Koch, were transferred into this confinement.

Six days following infestation with mites, the plants were examined for adult live mites remaining on the leaves to determine the percent control.

D. Rice Planthopper One-Day Residual Test

Test formulations of 1000 ppm concentration of compounds 1-63 were utilized. Two rice seedling plants were treated with each formulation by spraying with a spray atomizer. Ten adult rice planthoppers, *Sogatodes cryzicola*, were placed on plants in each pot one day following treatment. The surviving planthoppers were counted after five days to determine the percent control.

E. Tobacco Budworm Diet Test

Test formulations of compounds 1-63 were prepared at 3,000 or 6,000 ppm. Two-tenths ml of the formulation was pipetted onto the surface of 5 g of a synthetic diet mixture held in partially filled cells of a plastic jelly tray. Five cells were treated with the chemical dilution in this manner.

Following treatment, a third instar larva of the tobacco budworm, *Heliothis virescens*, was placed in each cell. At the end of one and two weeks, trays were examined and the percent control was determined.

The results of Tests A, B, C, D and E are summarized in Table III.

It should be noted that these abbreviations were used:
BW: Boll weevil (at 1000 ppm)
CR: Southern corn rootworm (at 1000 or 500* ppm)
MI: Mites (at 1000 ppm)
RPH: Rice plant hopper (at 1000 ppm)
TB: Tobacco budworm (at 6000 or 3000* ppm)

TABLE III

| Cpd No. | BW | CR | MI | RPH | TB |
|---|---|---|---|---|---|
| 1 | 100 | 100 | 30 | 100 | 58 |
| 2 | 67 | 100 | 25 | 0 | 0 |
| 3 | 90 | 100 | 0 | 70 | 100 |
| 4 | 0 | 0* | 0 | 0 | 20* |
| 5 | 37 | 78 | 0 | 0 | 20 |
| 6 | 47 | 55 | 0 | 0 | 60 |
| 7 | 28 | 60* | 0 | 40 | 16* |
| 8 | 17 | 0* | 60 | 60 | 8* |
| 9 | 100 | 32* | 85 | 40 | 58* |
| 10 | 83 | 10* | 0 | 90 | 20* |
| 11 | 100 | 32* | 80 | 90 | 16* |
| 12 | 83 | 100* | 0 | 60 | 100* |
| 13 | 0 | 54* | 0 | 0 | 0* |
| 14 | 67 | 0* | 0 | 70 | 0* |
| 15 | 79 | 80 | 0 | 0 | 100 |
| 16 | 100 | 40 | 90 | 75 | 100 |
| 17 | 100 | 100 | 95 | 100 | 60 |
| 18 | 0 | 11* | 0 | 0 | 0* |
| 19 | 88 | 0* | 0 | 0 | 80* |
| 21 | 0 | 11* | 0 | 0 | 0* |
| 22 | 100 | 75 | 0 | 40 | 100 |
| 23 | 100 | 100 | 0 | 10 | 79 |
| 24 | 88 | 100 | 80 | 0 | 47 |
| 25 | 26 | 100 | 0 | 50 | 0 |
| 26 | 100 | 80 | 50 | 0 | 20 |
| 27 | 100 | 60 | 0 | 90 | 0 |
| 28 | 100 | 0* | 80 | 100 | 60* |
| 29 | 0 | 0* | 80 | 0 | 100* |
| 30 | 50 | 80 | 0 | 0 | 0 |
| 31 | 88 | 60 | 0 | 30 | 80 |
| 32 | 0 | 16* | 0 | 0 | 0* |
| 33 | 89 | 100 | 0 | 60 | 100 |
| 34 | 14 | 72* | 0 | 0 | 0* |
| 35 | 0 | 0 | 0 | 70 | 0 |
| 36 | 100 | 0 | 0 | 0 | 0 |
| 37 | 100 | 100 | 0 | 0 | 0 |
| 38 | 100 | 0* | 0 | 0 | 20* |
| 39 | 16 | 0 | 0 | 95 | 40 |
| 40 | 0 | 0 | 0 | 95 | 0 |
| 41 | 100 | 100 | 15 | 90 | 20 |
| 42 | 100 | 44* | 0 | 0 | 0* |
| 43 | 100 | 100 | 0 | 100 | 100 |
| 44 | 75 | 100 | 0 | 100 | 0 |
| 45 | 100 | 100 | 15 | 50 | 20 |
| 46 | 71 | 100* | 0 | 0 | 25* |
| 47 | 0 | 33* | 0 | 0 | 0* |
| 48 | 100 | 100 | 0 | 0 | 100 |
| 49 | 100 | 100 | 0 | 0 | 100 |
| 50 | 100 | 75 | 0 | 0 | 0 |
| 51 | 100 | 50 | 0 | 0 | 0 |
| 52 | 100 | 100 | 0 | 50 | 0 |
| 53 | 100 | 100 | 0 | 95 | 0 |
| 54 | 100 | 80 | 0 | 50 | 0 |
| 55 | 73 | 79 | 25 | 90 | 53 |
| 56 | 100 | 75 | 90 | 95 | 0 |
| 57 | 100 | 100 | 0 | 0 | 0 |
| 58 | 0 | 100* | 0 | 50 | 0* |
| 59 | 50 | 100 | 0 | 70 | 20 |
| 60 | 87 | 100 | 25 | 30 | 0 |
| 61 | 100 | 100 | 0 | 4 | 67 |
| 62 | 100 | 100 | 90 | 50 | 100 |
| 63 | 33 | 100 | 20 | 80 | 20 |

EXAMPLE 5

NEMATOCIDAL USE OF THE COMPOUNDS OF THIS INVENTION

Certain species of compound (I) of this invention also exhibit nematocidal activity. Southern root-knot nematode, *Meloidogyne incognita*, was reared in sandy culture soil using tomato as a host plant. Roots from the culture plants were ground in a Waring blender. Ground roots and culture soils were mixed with equal parts of uninfested soil and the mixture was placed in pots. Test formulations were prepared at 1000 ppm. Twenty-five ml of the dilution were used to drench the pots, providing a soil concentration of 50 ppm. One day after treatment, two tomato seedlings were planted in each pot. Twelve days after planting, the soil was washed from roots, and treatments were evaluated by comparing the number of knots on plants roots from treated soil to those from the untreated nematode-infested control. The results are summarized in Table IV.

TABLE IV

| Cpd. No. | Nematocidal Activity % Control |
|---|---|
| 1 | 35 |
| 2 | 90 |
| 17 | 90 |
| 20 | 50 |
| 41 | 98 |
| 44 | 75 |
| 53 | 25 |
| 56 | 80 |

EXAMPLE 6

Control of Rice Planthopper

Two rice seedling plants in pots containing 600 grams of potting soil were treated by injecting with a syringe 30 ml of a 200 ppm suspension, in which compound 43 was the active agent, under the root system of the plant. The resulting soil concentration of the treatment was 10 ppm. One day after treatment ten (10) adult rice planthoppers, *Sogatodes oryzicola*, were placed on plants and confined to the plants using a plastic cylinder. The surviving planthoppers were counted 5 days after loading to determine the percent control (see Table IV).

TABLE IV

| Cpd No. | Rate PPM | % Control of Planthoppers |
|---|---|---|
| 43 | 10 | 65 |

The data indicate systemic pesticidal activity.

The examples and embodiments disclosed herein will make apparent to those skilled in the art other examples and embodiments within the scope and spirit of the instant invention. These examples and embodiments are within the contemplation of the instant invention. Therefore, the scope of the instant invention should be limited only by the appended claims.

What is claimed is:

1. A compound of the formula:

$$R-\underset{O}{\overset{N-N}{\underset{\|}{\bigwedge}}}-CH(R^1)-S-\overset{X}{\underset{\|}{P}}\overset{(YR^2)}{\underset{(ZR^2)}{\diagdown}}$$

wherein:

R is pyridyl or thienyl;

$R^1$ is hydrogen, $C_1-C_3$ alkyl, $C_7-C_9$ aralkyl, phenyl, $C_7-C_9$ aralkyl substituted with one member selected from the group consisting of halogen, $C_1-C_4$ alkyl, trihalomethyl, $C_1-C_4$ alkoxy, trihalomethoxy, trihalomethylthio, $C_1-C_4$ alkylthio, phenyl, phenoxy, cyano or nitro; or phenyl substituted with one member selected from the group consisting of halogen, $C_1-C_4$ alkyl, trihalomethyl, $C_1-C_4$ alkoxy, trihalomethoxy, trihalomethylthio, $C_1-C_4$ alkylthio, phenyl, phenoxy, cyano or nitro;

$R^2$ is $C_1-C_4$ alkyl, with a proviso that if $R^1$ is 4-chlorophenyl, $R^2$ is not isopropyl; and X, Y and Z are the same or different and are oxygen or sulfur.

2. A compound in accordance with claim 1 wherein R is pyridyl or thienyl; $R^1$ is hydrogen, methyl or phenyl; $R^2$ is ethyl; X is sulfur; Y is oxygen; and Z is oxygen.

3. A compound in accordance with claim 2 wherein R is pyrid-2-yl, pyrid-3-yl, or pyrid-4-yl; when $R^1$ is hydrogen or methyl, and $R^2$ is ethyl.

4. A compound of the formula:

$$R-\underset{O}{\overset{N-N}{\underset{\|}{\bigwedge}}}-CH(R^1)Cl$$

wherein:

R is pyridyl or thienyl; and $R^1$ is hydrogen, $C_1-C_3$ alkyl, $C_7-C_9$ aralkyl, phenyl, $C_7-C_9$ aralkyl substituted with one member selected from the group consisting of halogen, $C_1-C_4$ alkyl, trihalomethyl, $C_1-C_4$ alkoxy, trihalomethoxy, trihalomethylthio, $C_1-C_4$ alkylthio, phenyl, phenoxy, cyano or nitro; or phenyl substituted with one member selected from the group consisting of halogen, $C_1$14 $C_4$ alkyl, trihalomethyl, $C_1-C_4$ alkoxy, trihalomethoxy, trihalomethylthio, $C_1-C_4$ alkylthio, phenyl, phenoxy, cyano or nitro.

5. A compound in accordance with claim 4 wherein R is pyridyl or thienyl; and $R^1$ is hydrogen, methyl or phenyl.

6. A compound in accordance with claim 5 wherein R is pyrid-2-yl, pyrid-3-yl, or pyrid-4-yl; when $R^1$ is hydrogen or methyl, respectively.

7. A pesticidal composition comprising:

(1) a pesticidally effective amount of a compound of the formula $$R-\underset{O}{\overset{N-N}{\underset{\|}{\bigwedge}}}-CH(R^1)-S-\overset{X}{\underset{\|}{P}}\overset{(YR^2)}{\underset{(ZR^2)}{\diagdown}}$$

wherein:

R is pyridyl or thienyl; and $R^1$ is hydrogen, $C_1-C_3$ alkyl, $C_7-C_9$ aralkyl, phenyl, $C_7-C_9$ aralkyl substituted with one member selected from the group consisting of halogen, $C_1-C_4$ alkyl, trihalomethyl, $C_1-C_4$ alkoxy, trihalomethoxy, trihalomethylthio, $C_1-C_4$ alkylthio, phenyl, phenoxy, cyano or nitro; or phenyl substituted with one member selected from the group consisting of halogen, $C_1-C_4$ alkyl, trihalomethyl, $C_1-C_4$ alkoxy, trihalomethoxy, trihalomethylthio, $C_1-C_4$ alkylthio, phenyl, phenoxy, cyano or nitro;

$R^2$ is $C_1-C_4$ alkyl, with a proviso that if $R^1$ is 4-chlorophenyl, $R^2$ is not isopropyl; and X, Y and Z are the same or different and are oxygen or sulfur; and (2) in combination with an inert carrier therefor.

8. A composition in accordance with claim 7 wherein R in said formula is pyridyl or thienyl; $R^1$ is hydrogen, methyl or phenyl; $R^2$ is ethyl; X, is sulfur, Y is oxygen; and Z is oxygen.

9. A composition in accordance with claim 7 where R in said formula is pyrid-2-yl, pyrid-3-y, and pyrid-4-yl when $R^1$ is hydrogen or methyl, respectively; and $R^2$ is ethyl.

10. A method of controlling pests selected from amongst insects, nematodes or acarids comprising the direct application of a pesticidally effective amount of a compound of the formula to said pests

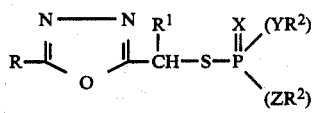

wherein:

R is pyrid or thienyl; and $R^1$ is hydrogen, $C_1$–$C_3$ alkyl, $C_7$–$C_9$ aralkyl, phenyl, $C_7$–$C_9$ aralkyl substituted with one member selected from the group consisting of halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro; or phenyl substituted with one member selected from the group consisting of halogen, $C_1$–$C_4$ alkyl, trihalomethyl, $C_1$–$C_4$ alkoxy, trihalomethoxy, trihalomethylthio, $C_1$–$C_4$ alkylthio, phenyl, phenoxy, cyano or nitro;

$R^2$ is $C_1$–$C_4$ alkyl, with a proviso that if $R^1$ is 4-chlorophenyl, $R^2$ is not isopropyl; and X, Y and Z are the same or different and are oxygen or sulfur.

11. A method in accordance with claim 10 wherein said pest is an insect and where an insecticidally effective amount of said compound is applied.

12. A method in accordance with claim 10 wherein said pest is a nematode and where a nematodicadal effective amount of said compound is applied.

13. A method in accordance with claim 10 wherein said pest is an acarid and where an acaricidal effective amount of said compound is applied.

14. A method in accordance with claim 10 wherein R in said formula is pyridyl or thienyl; $R^1$ is hydrogen or methyl or phenyl; $R^2$ is ethyl; X is sulfur, Y is oxygen; and Z is oxygen.

15. A method in accordance with claim 10 where R in said formula is pyrid-2-yl, pyrid-3-yl, or pyrid-4-yl when $R^1$ is hydrogen or methyl, and $R^2$ is ethyl.

* * * * *